(12) United States Patent
Chen et al.

(10) Patent No.: US 12,084,427 B2
(45) Date of Patent: Sep. 10, 2024

(54) METHOD FOR CONTINUOUSLY PREPARING N,N-BIS(2,2,6,6-TETRAMETHYL-4-PIPERIDYL)-1,6-HEXAMETHYL-ENEDIAMINE

(71) Applicant: Fudan University, Shanghai (CN)

(72) Inventors: Fener Chen, Shanghai (CN); Liangchuan Lai, Shanghai (CN); Baijun Ye, Shanghai (CN); Meifen Jiang, Shanghai (CN)

(73) Assignee: Fudan University, Shanghai (CN)

( * ) Notice: Subject to any disclaimer, the term of this patent is extended or adjusted under 35 U.S.C. 154(b) by 121 days.

(21) Appl. No.: 17/740,275

(22) Filed: May 9, 2022

(65) Prior Publication Data
US 2022/0281840 A1   Sep. 8, 2022

(51) Int. Cl.
C07D 401/12   (2006.01)
B01J 4/00   (2006.01)
B01J 8/02   (2006.01)

(52) U.S. Cl.
CPC ............ *C07D 401/12* (2013.01); *B01J 4/001* (2013.01); *B01J 4/008* (2013.01); *B01J 8/02* (2013.01)

(58) Field of Classification Search
CPC ......... C07D 401/12; B01J 4/001; B01J 4/008; B01J 8/02
See application file for complete search history.

(56) References Cited

U.S. PATENT DOCUMENTS

| 4,104,248 A | 8/1978 | Cantatore |
| 4,415,688 A | 11/1983 | Minagawa et al. |
| 4,605,743 A | 8/1986 | Malz, Jr. et al. |

FOREIGN PATENT DOCUMENTS

| CN | 1346825 A | 5/2002 | |
| CN | 104592097 A | 5/2015 | |
| JP | S619486 A | 1/1986 | |
| WO | WO-2015033266 A1 * | 3/2015 | .......... B01J 19/2485 |

OTHER PUBLICATIONS

Britton, Joshua, and Timothy F. Jamison. "The Assembly and Use of Continuous Flow Systems for Chemical Synthesis." Nature Protocols, vol. 12, No. 11, Oct. 2017, pp. 2423-2446. (Year: 2017).*
Parr Instrument Company. "5400MB Series 5400 Tubular Reactor Sales Literature." 5400 Continuous Flow Tubular Reactors Documents. https://www.parrinst.com/products/tubular-reactor-systems/5400-continuous-flow-tubular-reactors/documents-2/ (Year: 2021).*

* cited by examiner

*Primary Examiner* — Clinton A Brooks
*Assistant Examiner* — Jerica Katlynn Wilson

(57) ABSTRACT

Disclosed is a method of continuously preparing N,N-Bis (2,2,6,6-tetramethyl-4-piperidyl)-1,6-hexamethylenediamine, which relates to chemical engineering. The Pt/C catalyst and the quartz sand are mixed uniformly and loaded to the continuous-flow fixed-bed reactor. Then, hydrogen gas and a substrate solution containing 2,2,6,6-tetramethyl-4-piperidinone and 1,6-hexanediamine are simultaneously fed to the micro-mixer and the continuous-flow fixed-bed reactor in sequence to undergo a continuous catalytic reductive amination to obtain the N,N-Bis(2,2,6,6-tetramethyl-4-piperidyl)-1,6-hexamethylenediamine.

10 Claims, 1 Drawing Sheet

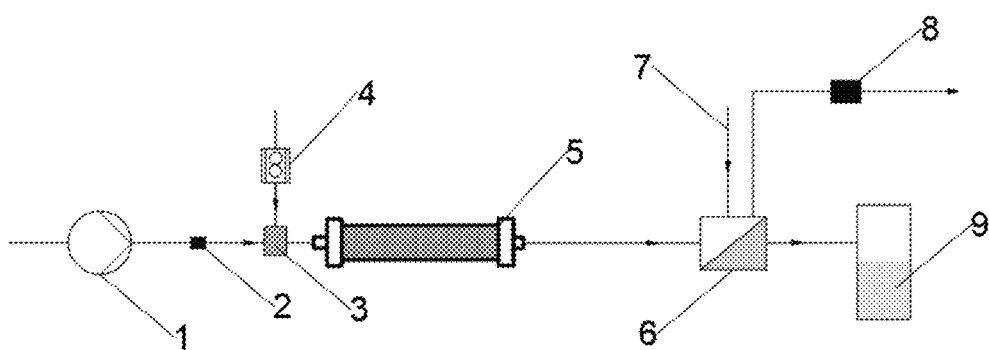

METHOD FOR CONTINUOUSLY PREPARING N,N-BIS(2,2,6,6-TETRAMETHYL-4-PIPERIDYL)-1,6-HEXAMETHYL-ENEDIAMINE

TECHNICAL FIELD

This application relates to chemical engineering, and more specifically to a method for continuously preparing N,N-Bis(2,2,6,6-tetramethyl-4-piperidyl)-1,6-hexamethyl-enediamine by using a continuous-flow micro-reaction system.

BACKGROUND

N,N-Bis(2,2,6,6-tetramethyl-4-piperidyl)-1,6-hexamethylenediamine (III) is an important intermediate in the production of hindered amine light stabilizers.

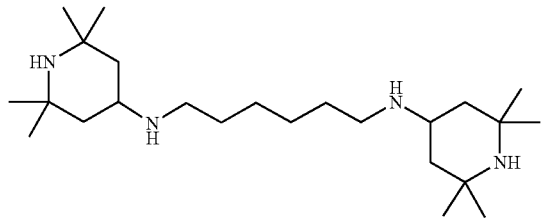

(III)

Chinese Patent Application Publication No. 1346825A discloses a method of preparing N, N-Bis(2,2,6,6-tetramethyl-4-piperidyl)-1,6-hexamethylenediamine in water, alcohol, or a combination thereof under a hydrogen pressure of 3-12 MPa. Unfortunately, this process requires high reaction pressure, which aggravates the safety hazard. Moreover, raw materials need to be premixed before the reaction, which prolongs the production period and raises costs. U.S. Patent Publication No. 4104248 reports a method of preparing N,N-Bis(2,2,6,6-tetramethyl-4-piperidyl)-1,6-hexamethylenediamine in methanol at 50 atm. Although this method has a yield up to 90%, it still requires a relatively high reaction pressure. U.S. Patent Publication No. 4605743A discloses a method of preparing N,N-Bis(2,2,6, 6-tetramethyl-4-piperidyl)-1,6-hexamethylenediamine in alcohol or a mixture of alcohol and water at a relatively low pressure (100-200 psi), in which an expensive Pd catalyst is adopted. As disclosed by U. S. Patent Publication No. 4415688A, the preparation is performed at a relatively low pressure (100-200 psi), but it involves complicated synthesis and separation procedures and a lower yield, and thus is not suitable for the industrial application.

In addition, Japanese Patent Publication No. 619486A discloses a method of preparing N,N-Bis(2,2,6,6-tetramethyl-4-piperidyl)-1,6-hexamethylenediamine from 2,2,6,6-tetramethyl-4-piperidinone and hexamethylene diamine under hydrogen in the presence of a hydrogenation catalyst (such as Pt), with a yield of merely 73%. As reported by Chinese Patent Publication No. 104592097A, hexamethylene diamine and 2,2,6,6-tetramethyl-4-piperidinone undergo a dehydration reaction to give a Schiff base intermediate, which further undergoes a hydrogenation reaction in the presence of a catalyst to form N,N-Bis(2,2,6,6-tetramethyl-4-piperidyl)-1,6-hexamethylenediamine. Nevertheless, the dehydration reaction generally involves a large consumption of methylbenzene or dimethylbenzene, which will cause a high production cost.

Hence, it is urgent for those skilled in the art to develop a continuous preparation method of N,N-Bis(2,2,6,6-tetramethyl-4-piperidyl)-1,6-hexamethylenediamine with a short reaction time, low energy consumption, high process efficiency and essential safety.

SUMMARY

An object of this application is to provide a method for continuously preparing N,N-Bis(2,2,6,6-tetramethyl-4-piperidyl)-1,6-hexamethylenediamine to overcome deficiencies in the prior art. The method provided herein has shortened reaction time, optimized degree of automation, improved production efficiency, lowered energy consumption and enhanced safety, and is thus suitable for the industrial application.

Technical solutions of this application are described as follows.

A first object of this application is to provide a method of continuously preparing N,N-Bis(2,2,6,6-tetramethyl-4-piperidyl)-1,6-hexamethylenediamine using a continuous flow micro-reaction system, the continuous flow micro-reaction system comprising a micro-mixer, a continuous flow fixed-bed reactor and a gas-liquid separator communicated in sequence; and the method comprising:

(S1) mixing a quartz sand with a Pt/C catalyst uniformly followed by feeding to the continuous-flow fixed-bed reactor; wherein the Pt/C catalyst is available commercially, and comprises 5% by weight of platinum;

(S2) feeding hydrogen gas and a substrate solution containing 2,2,6,6-tetramethyl-4-piperidinone (II) and 1,6-hexanediamine (I) to the micro-mixer for mixing to obtain a reaction mixture; and allowing the reaction mixture to flow into the continuous-flow fixed-bed reactor to undergo a continuous catalytic reductive amination; and (S3) collecting the reacting mixture flowing out from the continuous-flow fixed-bed reactor followed by gas-liquid separation in the gas-liquid separator, isolation and purification to obtain a target product N,N-Bis(2, 2,6,6-tetramethyl-4-piperidyl)-1,6-hexamethylenediamine (III);

as shown in the following reaction scheme:

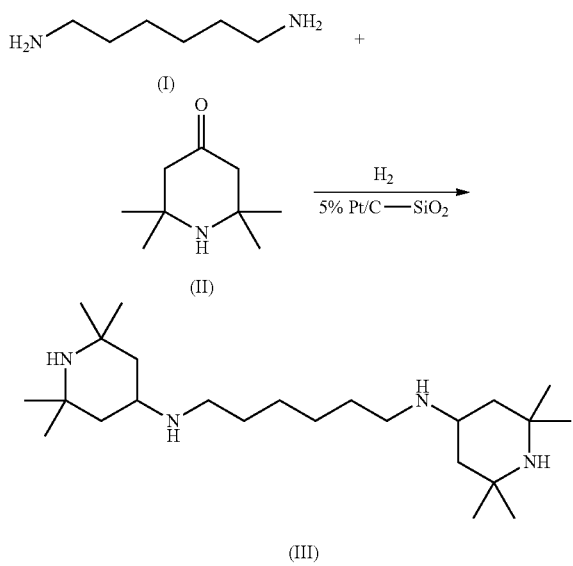

In an embodiment, in step (S1), the Pt/C catalyst is added into the quartz sand; and the Pt/C catalyst is 1-30% by weight of the quartz sand.

In an embodiment, the Pt/C catalyst and the quartz sand both have a particle size larger than 20 mesh, preferably larger than 60 mesh, allowing for a better mixing effect.

In an embodiment, in step (S1), the Pt/C catalyst is 1-25%, preferably 1-15%, by weight of the quartz sand.

In an embodiment, in step (S2), the substrate solution is prepared by dissolving 2,2,6,6-tetramethyl-4-piperidinone and 1,6-hexanediamine in an organic solvent; and the organic solvent is selected from the group consisting of methanol, ethanol, propanol, isopropanol, 1,2-propanediol, 1,3-propanediol, glycerol, n-butanol, sec-butanol, iso-butanol, tert-butanol, 1,2-butanediol, 1,3-butanediol, 1,4-butanediol, 1-pentanol, 2-pentanol, 3-pentanol, tert-pentanol, 1,2-pentanediol, 1,3-pentanediol, 1,4-pentanediol, 1,5-pentanediol, cyclopentanol, hexanol, cyclohexanol, heptanol, octanol, n-nonanol, decanol, ethylene glycol, diethylene glycol, polyethylene glycol, benzyl alcohol, phenol, toluene, xylene and a mixture thereof, preferably methanol, ethanol, n-propanol, isopropanol or n-butanol.

In an embodiment, a molar ratio of the 1,6-hexanediamine to the 2,2,6,6-tetramethyl-4-piperidinone is 1:(1.5-5), preferably 1:(2-3); and a concentration of the 1,6-hexanediamine in the substrate solution is 0.01-10 mol/L, preferably 0.1-6.5 mol/L.

In an embodiment, in step (S2), a flow ratio of the substrate solution to the hydrogen gas is adjusted such that a molar ratio of the substrate solution to the hydrogen gas in the micro-mixer is 1:(0.55-14).

In an embodiment, in step (S2), the micro-mixer is controlled at 20-180° C., preferably 20-150° C.

In an embodiment, in step (S2), the continuous-flow fixed-bed reactor is controlled at 20-180° C., preferably 60-150° C.

In an embodiment, a residence time of the reaction mixture in the continuous-flow fixed-bed reactor is controlled to 0.1-60 min, preferably 0.2-40 min.

In an embodiment, the micro-mixer is a static mixer, a T-type micro-mixer, a Y-type micro-mixer, a coaxial-flow micro-mixer or a flow-focusing micro-mixer.

In an embodiment, the continuous-flow fixed-bed reactor is composed of one or more tubular continuous-flow fixed-bed reactors connected in series or in parallel.

In an embodiment, an inner diameter of the one or more tubular continuous-flow fixed-bed reactors is 100 μm-50 mm, preferably 120 μm-30 mm.

In an embodiment, an $N_2$ is introduced into the gas-liquid separator at a pressure of 0.1-18 MPa, preferably 0.5-15 MPa; the continuous flow micro-reaction system further comprises a back-pressure valve; the back-pressure valve is connected to a port at a top of the gas-liquid separator; and a back pressure of the back-pressure valve is set to 0.1-15 MPa, preferably 0.5-15 MPa.

In an embodiment, in step (S3), the isolation and purification are performed through a step of:

subjecting the reacting mixture flowing out from the continuous-flow fixed-bed reactor to vacuum concentration, purification and drying to obtain the target product N,N-Bis(2,2,6,6-tetramethyl-4-piperidyl)-1,6-hexamethylenediamine.

In an embodiment, the feeding pump is configured to feed a substrate solution containing 2,2,6,6-tetramethyl-4-piperidinone and 1,6-hexanediamine to the micro-mixer; the gas mass-flow meter is configured to feed the hydrogen gas to the micro-mixer; the substrate solution and the hydrogen gas are mixed in the micro-mixer, and flow into the continuous-flow fixed-bed reactor to undergo a continuous catalytic reductive amination reaction; the reacting mixture flowing out of the continuous-flow fixed-bed reactor flows into the condenser to be condensed, and then enters the gas-liquid separator to undergo gas-liquid separation, where waste gas is discharged through a port arranged on a top of the gas-liquid separator and the back-pressure valve, and the reacting mixture is discharged from an outlet at a bottom of the gas-liquid separator and collected, and subjected to isolation and purification to obtain a target product N,N-Bis (2,2,6,6-tetramethyl-4-piperidyl)-1,6-hexamethylenediamine.

Compared with the prior art, this application has the following beneficial effects.

The preparation method provided herein employs a micro-reaction system including a micro-mixer and a continuous-flow fixed-bed reactor successively communicated. Compared with the existing synthetic method using a conventional batch reactor, the method provided herein has the following advantages.

(1) The method provided herein enables the continuous synthesis of the target product in the absence of external intervention, and has high degree of automation and excellent space-time efficiency, which can greatly reduce the labor force and intensity, and significantly lower the production cost.

(2) The continuous catalytic reductive amination reaction between the 1,6-hexanediamine and the 2,2,6,6-tetramethyl-4-piperidinone is completed in a reaction fluid channel of the continuous-flow fixed-bed reactor, which allows a small online liquid holdup due to the small volume of the reaction fluid channel, ensuring that the reaction process is essentially safe.

(3) The continuous flow fixed-bed reactor has excellent mass and heat transfer performances and mixing performance, which greatly reduces the continuous amination reaction time of the 1,6-hexamediamine and the 2,2,6,6-tetramethyl-4-piperidinone to several minutes, while the traditional batch reactors require several hours.

(4) Based on the continuous flow process of the continuous flow fixed-bed reactor, there is no need to remove the catalyst from the reaction liquid. In this case, the reaction system can run continuously for a long time, which can greatly improve the process efficiency and space-time efficiency, resulting in a high product yield (>90%). Moreover, the time consumption, labor intensity and processing cost are reduced.

(5) The multiphase mixing, mass transfer, and reaction processes are completed in the micro-mixer and the reaction fluid channel of the continuous flow fixed-bed reactor in the absence of a stirring device, which greatly reduces the energy consumption of the process.

BRIEF DESCRIPTION OF THE DRAWINGS

This FIGURE schematically illustrates a structure of a continuous flow micro-reaction system according to an embodiment of the present disclosure.

In the drawing, 1, feeding pump; 2, one-way valve; 3, micro-mixer; 4, gas mass-flow meter; 5, continuous-flow fixed-bed reactor; 6, gas-liquid separator; 7, nitrogen gas pipeline; 8, back-pressure valve; and 9, storage tank.

DETAILED DESCRIPTION OF EMBODIMENTS

This application will be described in detail below with reference to the embodiments to make objects, technical solutions and advantages of this application clearer.

A continuous flow micro-reaction system used herein is structurally depicted in FIG. 1, which includes a feeding pump 1, a one-way valve 2, a micro-mixer 3, a gas mass-flow meter 4, a continuous-flow fixed-bed reactor 5, a gas-liquid separator 6, a nitrogen gas channel 7, a back-pressure valve 8, and a storage tank 9.

One inlet of the micro-mixer 3 is connected to the gas mass-flow meter 4, and the other inlet of the micro-mixer 3 is connected to an outlet of the one-way valve 2. An inlet of the one-way valve 2 is connected to the feeding pump 1. An inlet of the continuous-flow fixed-bed reactor 5 is connected to an outlet of the micro-mixer 3, and an outlet of the continuous-flow fixed-bed reactor 5 is connected to a first port at a top of the gas-liquid separator 6. A second port at the top of the gas-liquid separator 6 is connected to the nitrogen gas pipeline 7 for $N_2$ introduction. The back-pressure valve 8 is connected to a third port at the top of the gas-liquid separator 6. An outlet at a bottom of the gas-liquid separator 6 is connected to the storage tank 9.

The continuous flow micro-reaction system is operated as follows.

(S1) A Pt/C catalyst (containing 5% by weight of Pt) and a quartz sand are mixed uniformly and then fed to the continuous-flow fixed-bed reactor 5. A substrate solution containing the 2,2,6,6-tetramethyl-4-piperidinone and the 1,6-hexanediamine is prepared.

(S2) The substrate solution and hydrogen gas are fed to the micro-mixer 3 by using the feeding pump 1 and the gas mass-flow meter 4, respectively, mixed and then flow into the continuous-flow fixed-bed reactor 5 to undergo a continuous catalytic reductive amination reaction. Then the reacting mixture flows into the gas-liquid separator 6 to undergo gas-liquid separation, where waste gas is discharged through the third port at the top of the gas-liquid separator 6 and the back-pressure valve 8, and the reaction mixture is discharged from the outlet at the bottom of the gas-liquid separator 6, collected and subjected to isolation and purification to obtain the target product N,N-Bis(2,2,6,6-tetramethyl-4-piperidyl)-1,6-hexamethylenediamine.

Example 1

(1) Preparation of Catalyst

A Pt/C catalyst (containing 5% by weight of Pt) was added into the quartz sand and stirred for uniform mixing, where the Pt/C catalyst was 15% by weight of the quartz sand.

(2) Catalytic Hydrogenation

The Pt/C catalyst-quartz sand mixture was loaded to a tubular continuous-flow fixed-bed reactor with a length of 20 cm and an inner diameter of 2 cm. 4 g of 1,6-hexanediamine and 8.41 g of 2,2,6,6-tetramethyl-4-piperidinone was added to 90 mL of methanol to prepare a substrate solution. After that, hydrogen gas and the substrate solution were simultaneously fed to a coaxial-flow micro-mixer, in which the temperature was controlled to 80° C. A flow ratio of the substrate solution to the hydrogen gas was adjusted such that a molar ratio of the substrate solution to the hydrogen gas was 1:2.1. The substrate solution and hydrogen were mixed via a T-type micro-mixer, and the reaction mixture was fed to the tubular continuous-flow fixed-bed reactor and reacted for 8 min, where a reaction volume in the tubular continuous-flow fixed-bed reactor was about 2 mL; a back-pressure value of the back-pressure valve was set to 4.0 MPa; an internal temperature of the tubular continuous-flow fixed-bed reactor was controlled to 80° C. After the reaction is completed, the reacted mixture was allowed to flow out of the tubular continuous-flow fixed-bed reactor and enter the gas-liquid separator for gas-liquid separation, where gas components were removed, and the reaction mixture was collected to the storage tank. Then the reaction mixture was subjected concentration, purification, and drying to obtain a white solid N,N-Bis(2,2,6,6-tetramethyl-4-piperidyl)-1,6-hexamethylenediamine with a purity over 98.5% (90% yield). The analysis results demonstrated that the substrate 1,6-hexamethylenediamine experienced a complete conversion.

Example 2

The preparation method provided in Example 2 was basically the same as that in Example 1 except that in this example, the hydrogen gas and the substrate solution were mixed in a T-type micro-mixer. In this example, the substrate 1,6-hexamethylenediamine experienced a complete conversion, and the target product N,N-Bis(2,2,6,6-tetramethyl-4-piperidyl)-1,6-hexamethylenediamine had a yield of 85% and a purity over 98.5%.

Example 3

The preparation method provided in Example 3 was basically the same as that in Example 1 except that in this example, the Pt/C catalyst was 5% by weight of the quartz sand. In this example, the substrate 1,6-hexamethylenediamine experienced a complete conversion, and the target product N,N-Bis(2,2,6,6-tetramethyl-4-piperidyl)-1,6-hexamethylenediamine had a yield of the 80% and a purity over 98%.

Example 4

The preparation method provided in Example 4 was basically the same as that in Example 1 except that in this example, the continuous-flow fixed-bed reactor was composed of two tubular fixed-bed reactors connected in parallel, and the reaction time was 10 min. In this example, the substrate 1,6-hexamethylenediamine experienced a complete conversion, the target product N,N-Bis(2,2,6,6-tetramethyl-4-piperidyl)-1,6-hexamethylenediamine had a yield of 95% and a purity over 98%.

Example 5

The preparation method provided in Example 5 was basically the same as that in Example 1 except that in this example, the hydrogen gas and the substrate solution were mixed in the Y-type micro-mixer. In this example, the substrate 1,6-hexamethylenediamine experienced a complete conversion, and the target product N,N-Bis(2,2,6,6-tetramethyl-4-piperidyl)-1,6-hexamethylenediamine had a yield of 85% and a purity over 98%.

Example 6

The preparation method provided in Example 6 was basically the same as that in Example 1 except that in this example, the molar ratio of the 1,6-hexanediamine to the 2,2,6,6-tetramethyl-4-piperidinone was 1:4, and the continuous-flow fixed-bed reactor was controlled to 100° C. In this embodiment, the substrate 1,6-hexamethylenediamine was completely transformed, and the target product N,N-Bis(2,2,6,6-tetramethyl-4-piperidyl)-1,6-hexamethylenediamine had a yield of 93% and a purity over 98%.

Example 7

The preparation method provided in Example 7 was basically the same as that in Example 1 except that in this example, the hydrogen gas and the substrate solution were mixed in the flow-focus micro-mixer. In this example, the substrate 1,6-hexamethylenediamine experienced a complete conversion, and the target product N,N-Bis(2,2,6,6-tetramethyl-4-piperidyl)-1,6-hexamethylenediamine had a yield of 94% and a purity over 98%.

Example 8

The preparation method provided in Example 8 was basically the same as that in Example 1 except that in this example, the molar ratio of the 1,6-hexanediamine to the 2,2,6,6-tetramethyl-4-piperidinone was 1:1.8, and the continuous-flow fixed-bed reactor was controlled to 70° C. In this example, the substrate 1,6-hexamethylenediamine experienced a complete conversion, and the the target product N,N-Bis(2,2,6,6-tetramethyl-4-piperidyl)-1,6-hexamethylenediamine had a yield of 65% and a purity over 95%.

Example 9

The preparation method provided in Example 9 was basically the same as that in Example except that in this example, the continuous-flow fixed-bed reactor was controlled to 120° C. In this example, the substrate 1,6-hexamethylenediamine experienced a complete conversion, and the target product N,N-Bis(2,2,6,6-tetramethyl-4-piperidyl)-1,6-hexamethylenediamine had a yield of 66% and a purity over 89%.

Example 10

The preparation method provided in Example 10 was basically the same as that in Example 1 except that in this example, the inner diameter of the continuous-flow fixed-bed reactor was 2.5 mm. In this example, the substrate 1,6-hexamethylenediamine experienced a complete conversion, and the target product N,N-Bis(2,2,6,6-tetramethyl-4-piperidyl)-1,6-hexamethylenediamine had a yield of 90% and a purity over 98%.

Example 11

The preparation method provided in Example 11 was basically the same as that in Example 1 except that in this example, the back-pressure value of the back-pressure valve was set to 3.0 Mpa, and the internal temperature of the continuous-flow fixed-bed reactor was controlled to 70° C. In this example, the substrate 1,6-hexamethylenediamine experienced a complete conversion, and the target product N,N-Bis(2,2,6,6-tetramethyl-4-piperidyl)-1,6-hexamethylenediamine had a yield of 87% and a purity over 98%.

Example 12

The preparation method provided in Example 12 was basically the same as that in Example 1 except that in this example, the substrate solution was prepared from 4 g of 1,6-hexanediamine, 8.21 g of 2,2,6,6-tetramethyl-4-piperidinone, and 300 mL of a mixture of methanol and ethanol. In this example, the substrate 1,6-hexamethylenediamine experienced a complete conversion, and the target product N,N-Bis(2,2,6,6-tetramethyl-4-piperidyl)-1,6-hexamethylenediamine had a yield of 83% and a purity over 98%.

Example 13

The preparation method provided in Example 13 was basically the same as that in Example 1 except that in this example, the substrate solution was prepared from 4 g of 1,6-hexanediamine, 8.05 g of 2,2,6,6-tetramethyl-4-piperidinone, and 40 mL of ethanol. In this example, the substrate 1,6-hexamethylenediamine experienced a complete conversion, and the target product N,N-Bis(2,2,6,6-tetramethyl-4-piperidyl)-1,6-hexamethylenediamine had a yield of 82.6% and a purity over 95%.

Example 14

The preparation method provided in Example 14 was basically the same as that in Example 1 except that in this example, the substrate solution was prepared from 30 g of 1,6-hexanediamine, 84.1 g of 2,2,6,6-tetramethyl-4-piperidinone and 1.5 L of methanol. In this example, the continuous-flow fixed-bed reactor was composed of two tubular fixed-bed reactors connected in parallel, and the reaction time was 20 min. In this example, the substrate 1,6-hexamethylenediamine experienced a complete conversion, and the target product N,N-Bis(2,2,6,6-tetramethyl-4-piperidyl)-1,6-hexamethylenediamine had a yield of 90% and a purity over 98%.

Example 15

The preparation method provided in Example 15 was basically the same as that in Example 1 except that in this example, the substrate solution was prepared from 4 g of 1,6-hexanediamine, 8.21 g of 2,2,6,6-tetramethyl-4-piperidinone and 120 ml of a mixture consisting of ethylene glycol and methanol. In this example, the substrate 1,6-hexamethylenediamine experienced a complete conversion, and the target product N,N-Bis(2,2,6,6-tetramethyl-4-piperidyl)-1,6-hexamethylenediamine had a yield of 92.1% and a purity over 98%.

Example 16

The preparation method provided in Example 16 was basically the same as that in Example 1 except that in this example, the substrate solution was prepared from 40 g of 1,6-hexanediamine, 80.5 g of 2,2,6,6-tetramethyl-4-piperidinone and 150 ml of methanol. In this example, the substrate 1,6-hexamethylenediamine experienced a complete conversion, and the target product N,N-Bis(2,2,6,6-tetramethyl-4-piperidyl)-1,6-hexamethylenediamine had a yield of 93% and a purity over 98%.

Comparative Example 1

Provided herein was a method of preparing N,N-Bis(2,2,6,6-tetramethyl-4-piperidyl)-1,6-hexamethylenediamine by using a traditional batch reactor. Specifically, 50 mL of methanol was added with 3 g of 1,6-hexanediamine and 8.41 g of 2,2,6,6-tetramethyl-4-piperidinone to prepare a substrate solution. A Pt/C catalyst containing 5% by weight of Pt and the substrate solution were transferred to a batch reactor. The hydrogen gas inlet valve was opened to adjust a pressure in the batch reactor to 5.0 MPa. The reaction mixture was heated to 80° C., and reacted under stirring at 900 r/min for 12 h, where the reaction mixture was sampled regularly for analysis. After the reaction was completed, the substrate 1,6-hexamethylenediamine experienced a complete conversion, and the target product N,N-Bis(2,2,6,6-tetramethyl-4-piperidyl)-1,6-hexamethylenediamine had a yield of 82% and a purity over 98.5%.

The feeding ratio of raw materials in Comparative Example 1 was the same as that in Example 1. Compared with Comparative Example 1, the method provided in Example 1 had a shorter reaction time and a higher yield (more than 90%) in the absence of a stirring device, resulting in lower energy consumption. In addition, the method provided in Example 1 enabled the continuous synthesis of the target product and had a simple operation, high degree of automation and excellent efficiency. Moreover, the method provided in Example 1 had a small online liquid holdup, excellent mass and heat transfer characteristics, making the process intrinsically safe and effectively avoiding the large safety hazard of catalytic hydrogenation by using the traditional batch reactor.

It should be noted that the above examples are only used to illustrate the technical solutions of the disclosure, and are not intended to limit the scope of the disclosure. It should be understood that any modifications, replacements and changes made by those skilled in the art without departing from the scope of the disclosure defined by the appended claims.

What is claimed is:

1. A method of continuously preparing N,N-Bis(2,2,6,6-tetramethyl-4-piperidyl)-1,6-hexamethylenediamine using a continuous flow micro-reaction system, the continuous flow micro-reaction system comprising a micro-mixer, a continuous flow fixed-bed reactor and a gas-liquid separator communicated in sequence; and the method comprising:
   (S1) mixing a quartz sand with a Pt/C catalyst uniformly followed by feeding to the continuous-flow fixed-bed reactor;
   (S2) feeding hydrogen gas and a substrate solution containing 2,2,6,6-tetramethyl-4-piperidinone (II) and 1,6-hexanediamine (I) to the micro-mixer for mixing to obtain a reaction mixture; and allowing the reaction mixture to flow into the continuous-flow fixed-bed reactor to undergo a continuous catalytic reductive amination reaction; wherein a flow ratio of the substrate solution to the hydrogen gas is adjusted such that a molar ratio of the substrate solution to the hydrogen gas in the micro-mixer is 1:(0.55-14); and
   (S3) collecting the reacting mixture flowing out from the continuous-flow fixed-bed reactor followed by gas-liquid separation in the gas-liquid separator, isolation and purification 10 obtain target product N,N-Bis(2,2,6,6-tetramethyl-4-piperidyl)-1,6-hexamethylenediamine (III); as shown in the following reaction scheme:

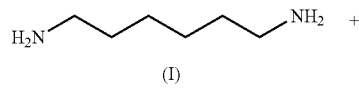

(I)

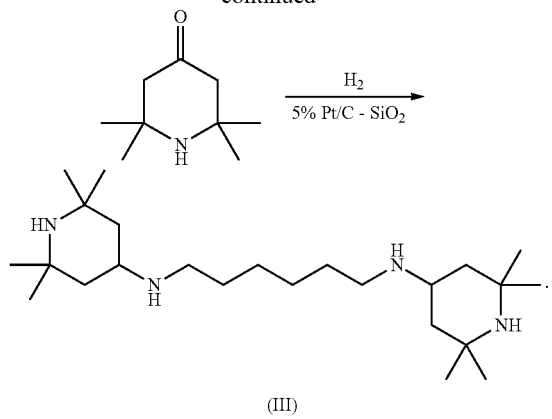

(III)

2. The method of claim 1, wherein in step (S1), the Pt/C catalyst is added into the quartz sand; and the Pt/C catalyst is 1-30% by weight of the quartz sand; the Pt/C catalyst and the quartz sand both have a particle size larger than 20 mesh.

3. The method of claim 1, wherein in step (S2), the substrate solution is prepared by dissolving 2,2,6,6-tetramethyl-4-piperidinone and 1, 6-hexanediamine in an organic solvent; and
   the organic solvent is selected from the group consisting of methanol, ethanol, propanol, isopropanol, 1,2-propanediol, 1,3-propanediol, glycerol, n-butanol, sec-butanol, isobutanol, tert-butanol, 1,2-butanediol, 1,3-butanediol, 1,4-butanediol, 1-pentanol, 2-pentanol, 3-pentanol, tert-pentanol, 1,2-pentanediol, 1,3-pentanediol, 1,4-pentanediol, 1,5-pentanediol, cyclopentanol, hexanol, cyclohexanol, heptanol, octanol, n-nonanol, decanol, ethylene glycol, diethylene glycol, polyethylene glycol, benzyl alcohol, phenol, toluene, xylene and a mixture thereof.

4. The method of claim 3, wherein a molar ratio of the 1,6-hexanediamine to the 2,2,6,6-tetramethyl-4-piperidinone is 1:(1.5-5); and a concentration of the 1,6-hexanediamine in the substrate solution is 0.01-10 mol/L.

5. The method of claim 1, wherein in step (S2), the micro-mixer and the continuous-flow fixed-bed reactor are both controlled at 20-180° C.

6. The method of claim 1, wherein in step (S2), a residence time of the reaction mixture in the continuous-flow fixed-bed reactor is controlled to 0.1-60 min.

7. The method of claim 1, wherein the micro-mixer is a static mixer, a T-type micro-mixer, a Y-type micro-mixer, a coaxial-flow micro-mixer or a flow-focusing micro-mixer.

8. The method of claim 1, wherein the continuous-flow fixed-bed reactor is composed of one or more tubular continuous-flow fixed-bed reactors connected in series or in parallel; and an inner diameter of the one or more tubular continuous-flow fixed-bed reactors is 100 μm-50 mm.

9. The method of claim 1, wherein $N_2$ is introduced into the gas-liquid separator at a pressure of 0.1-18 MPa; the continuous flow micro-reaction system further comprises a back-pressure valve; the back-pressure valve is connected to a port at the top of the gas-liquid separator; and the back pressure of the back-pressure valve is set to 0.1-15 MPa.

10. A continuous flow micro-reaction system for continuously preparing N,N-Bis(2,2,6,6-tetramethyl-4-piperidyl)-1,6-hexamethylenediamine, comprising:
   a feeding pump;
   a gas mass-flow meter having a flow controller;
   a one-way valve;

a micro-mixer;
a continuous-flow fixed-bed reactor;
a condenser;
a gas-liquid separator; and
a back-pressure valve;
wherein the continuous-flow fixed-bed reactor is filled with a Pt/C catalyst mixed uniformly with a quartz sand; and the Pt/C catalyst comprises 5% by weight of Pt;
the feeding pump is configured to feed a substrate solution containing 2,2,6,6-tetramethyl-4-piperidinone and 1,6-hexanediamine to the micro-mixer; the gas mass-flow meter is configured to feed hydrogen gas to the micro-mixer; the substrate solution and the hydrogen gas are mixed in the micro-mixer, and then flow into the continuous-flow fixed-bed reactor to undergo a continuous catalytic reductive amination reaction; the reacting mixture flowing out of the continuous-flow fixed-bed reactor flows into the condenser to be condensed, and then enters the gas-liquid separator to undergo gas-liquid separation, where waste gas is discharged through a port arranged on a top of the gas-liquid separator and the back-pressure valve, and the reaction mixture is discharged from an outlet at a bottom of the gas-liquid separator and collected, and subjected to isolation and purification to obtain a target product N,N-Bis(2,2,6,6-tetramethyl-4-piperidyl)-1,6-hexamethylenediamine.

* * * * *